(12) United States Patent
Lo et al.

(10) Patent No.: US 11,180,789 B2
(45) Date of Patent: Nov. 23, 2021

(54) METHOD FOR BIOCONVERSION OF MOGROSIDE EXTRACTS INTO SIAMENOSIDE I

(71) Applicant: National Taiwan University, Taipei (TW)

(72) Inventors: Yi-Chen Lo, Taipei (TW); Ting-Jang Lu, Taipei (TW); Reuben Wang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 75 days.

(21) Appl. No.: 16/584,216

(22) Filed: Sep. 26, 2019

(65) Prior Publication Data
US 2021/0095326 A1    Apr. 1, 2021

(51) Int. Cl.
*C12P 19/14* (2006.01)
*C12N 9/24* (2006.01)
*C12N 1/19* (2006.01)
*C12P 33/20* (2006.01)

(52) U.S. Cl.
CPC ............ *C12P 33/20* (2013.01); *C12N 9/2402* (2013.01)

(58) Field of Classification Search
None
See application file for complete search history.

(56) References Cited

FOREIGN PATENT DOCUMENTS

WO    WO-2012068832 A1 *  5/2012  ............... C12P 19/56
WO    WO-2014150127 A1 *  9/2014  ............... A23L 2/60

OTHER PUBLICATIONS

Crauwels et al., Appl. Environ. Microbiol. 80:4398-4413, 2014 (Year: 2014).*
Kuo et al., J. Food Drug Anal. 26:163-171, Jan. 2018 (Year: 2018).*
Machine translation of WO 2012/068832 A1, obtained from Google Patents on Apr. 15, 2021, 9 pages (Year: 2021).*
Reuben Wang et al., "*Dekkera bruxellensis*, a beer yeast that specifically bioconverts mogroside extracts into the intense natural sweetener siamenoside I"; Food Chemistry, Sep. 29, 2018, pp. 43-49.

* cited by examiner

*Primary Examiner* — David Steadman
(74) *Attorney, Agent, or Firm* — Muncy, Geissler, Olds and Lowe, P.C.

(57) ABSTRACT

The present invention provides a method for bioconversion of mogroside extracts into siamenoside I, comprising: using (1) DbExg1 protein or (2) a microorganism expressing the DbExg1 protein to contact or to cultivate with the mogroside extracts. The present invention can convert the mogroside extracts into siamenoside I, which has a higher sweetening power and better taste than other mogrosides. The method of the present invention uses a microorganism expressing the responsible enzyme, DbExg1, which was identified as a mediator of mogroside V conversion into siamenoside I in the present invention, so that siamenoside I was preferentially produced. Thus, the use of the method of the present invention provides a feasible approach to produce large quantities of the natural sweetener, siamenoside I, which can then be applied in several industries.

10 Claims, 7 Drawing Sheets

Specification includes a Sequence Listing.

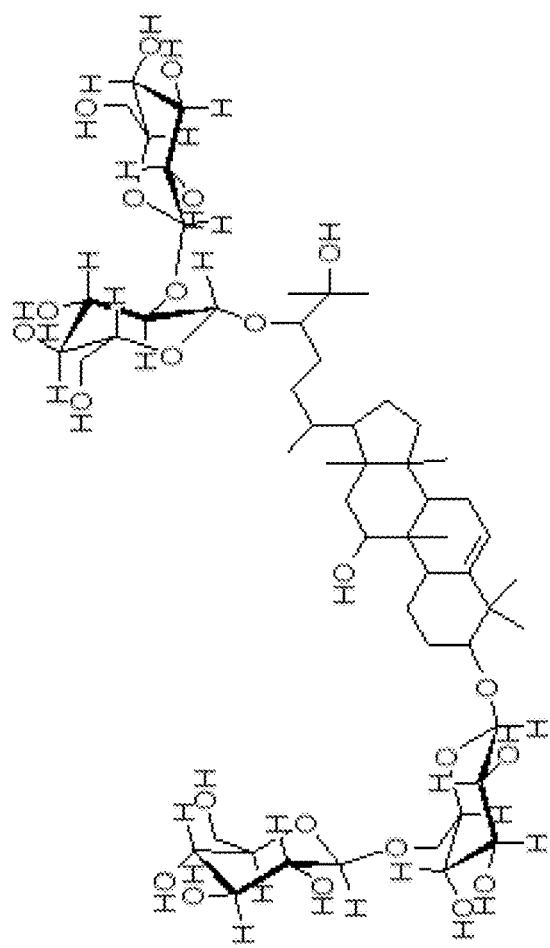
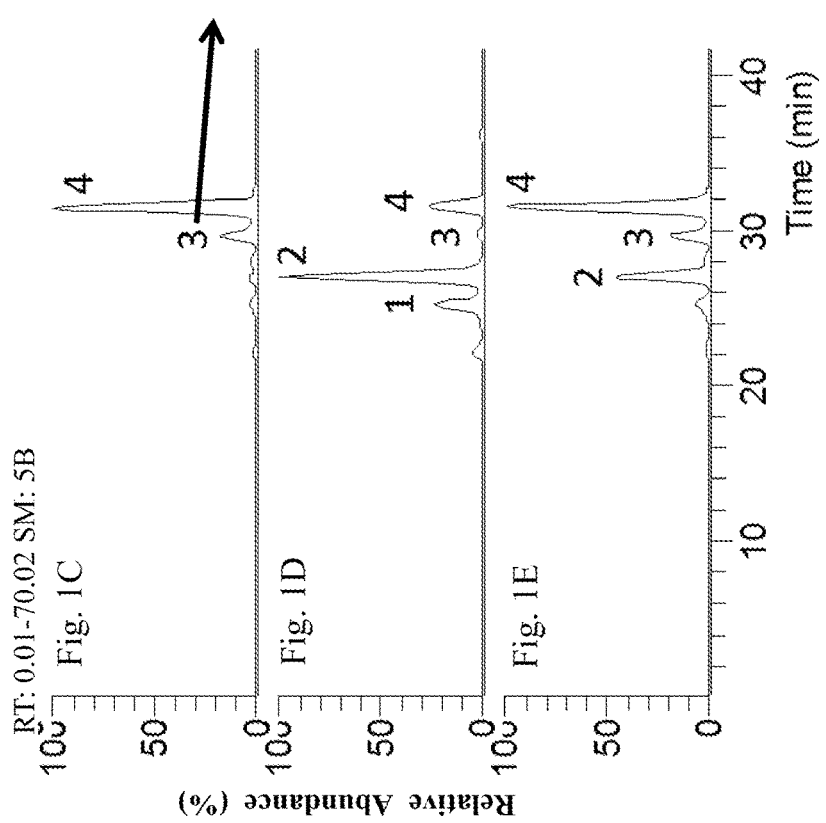
Fig. 1C
Fig. 1D
Fig. 1E

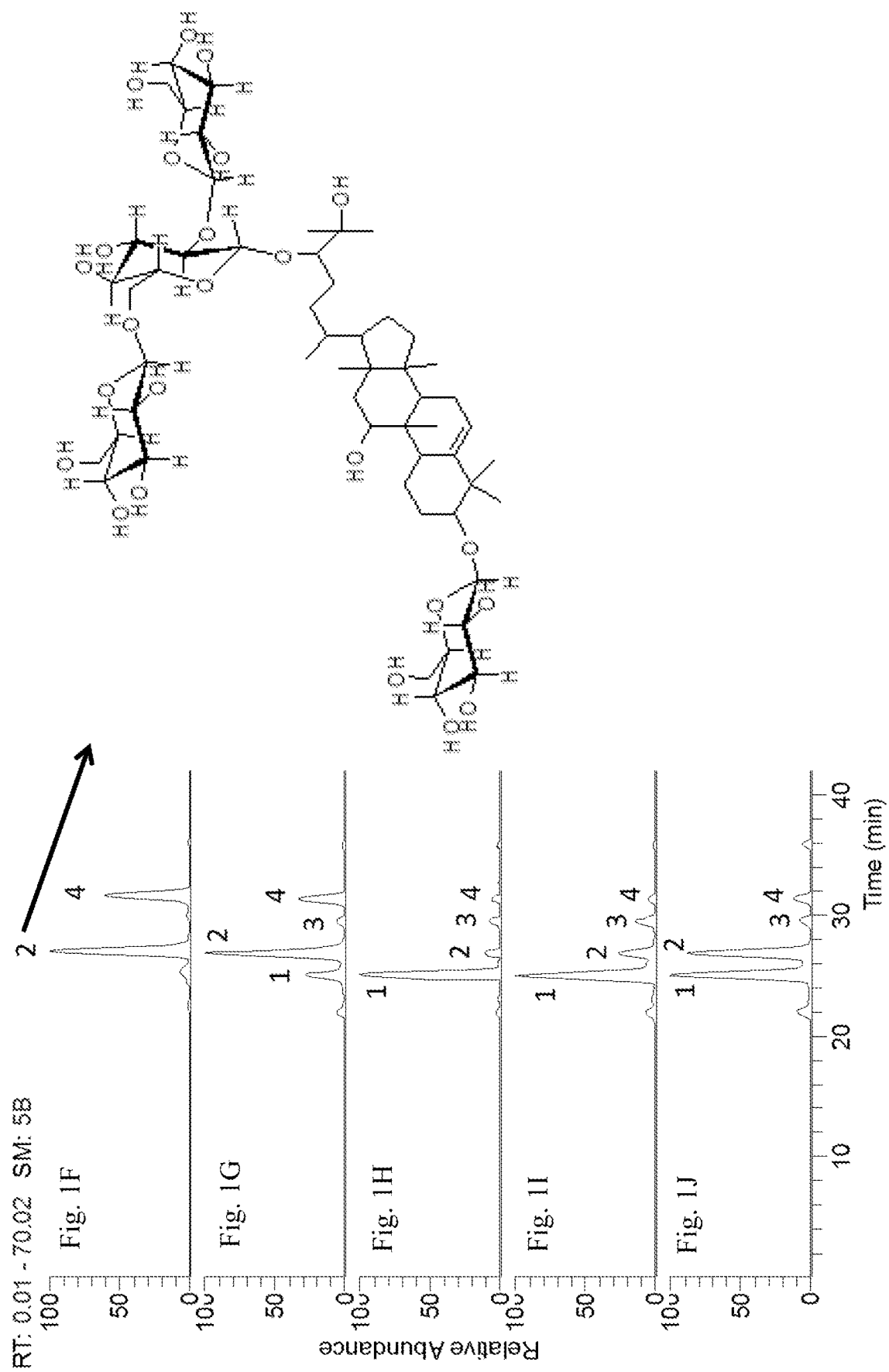

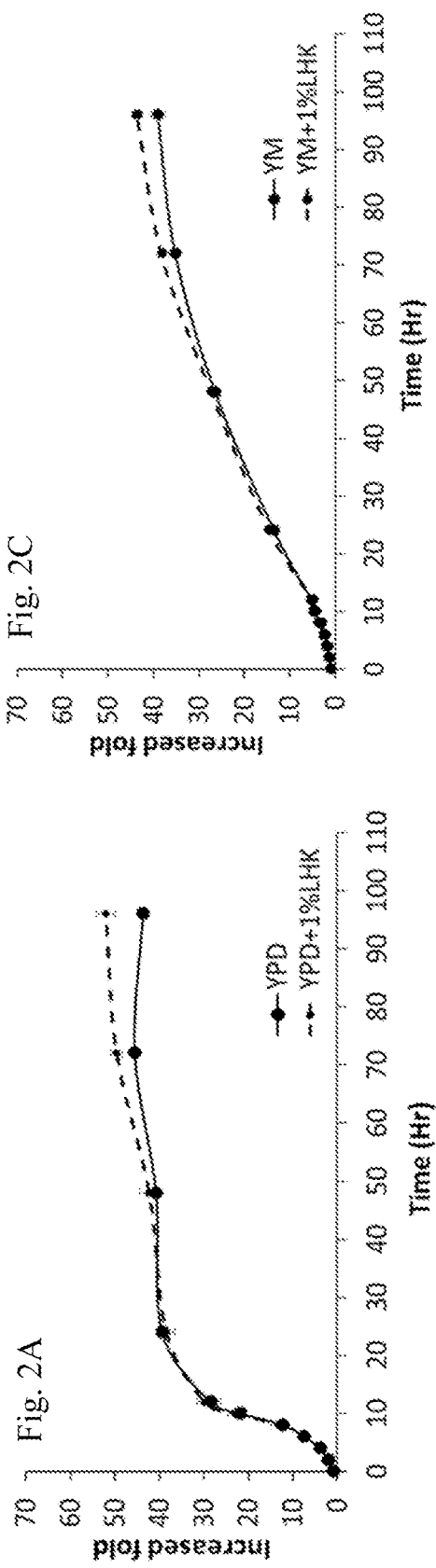
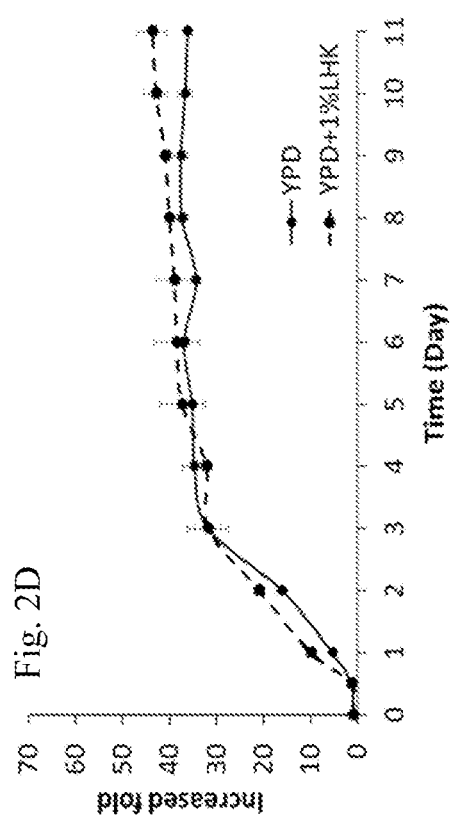
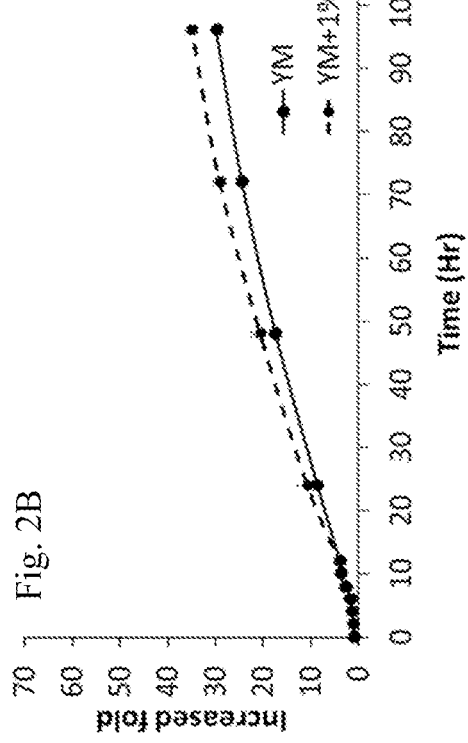
Fig. 2A
Fig. 2B
Fig. 2C
Fig. 2D

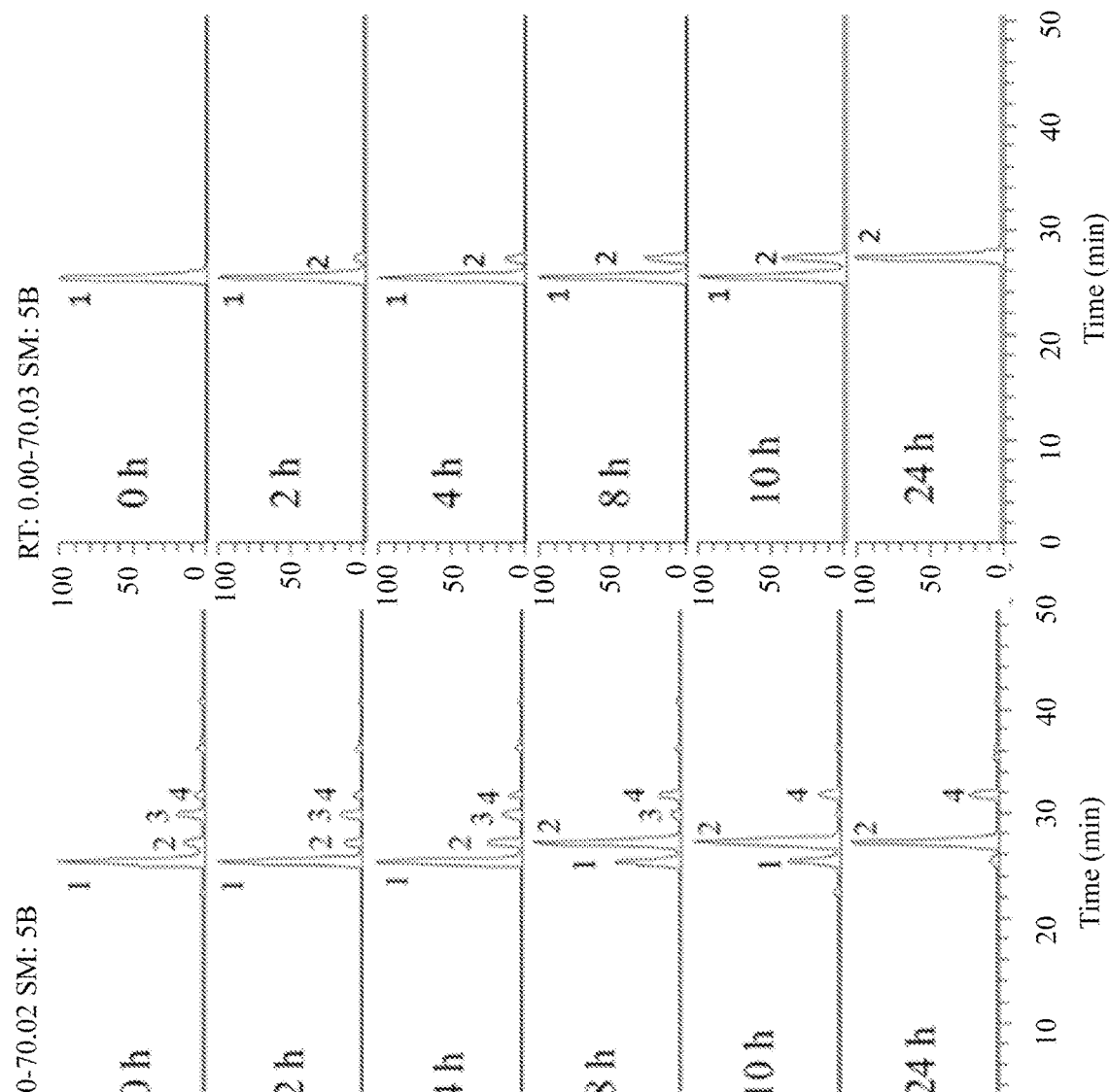

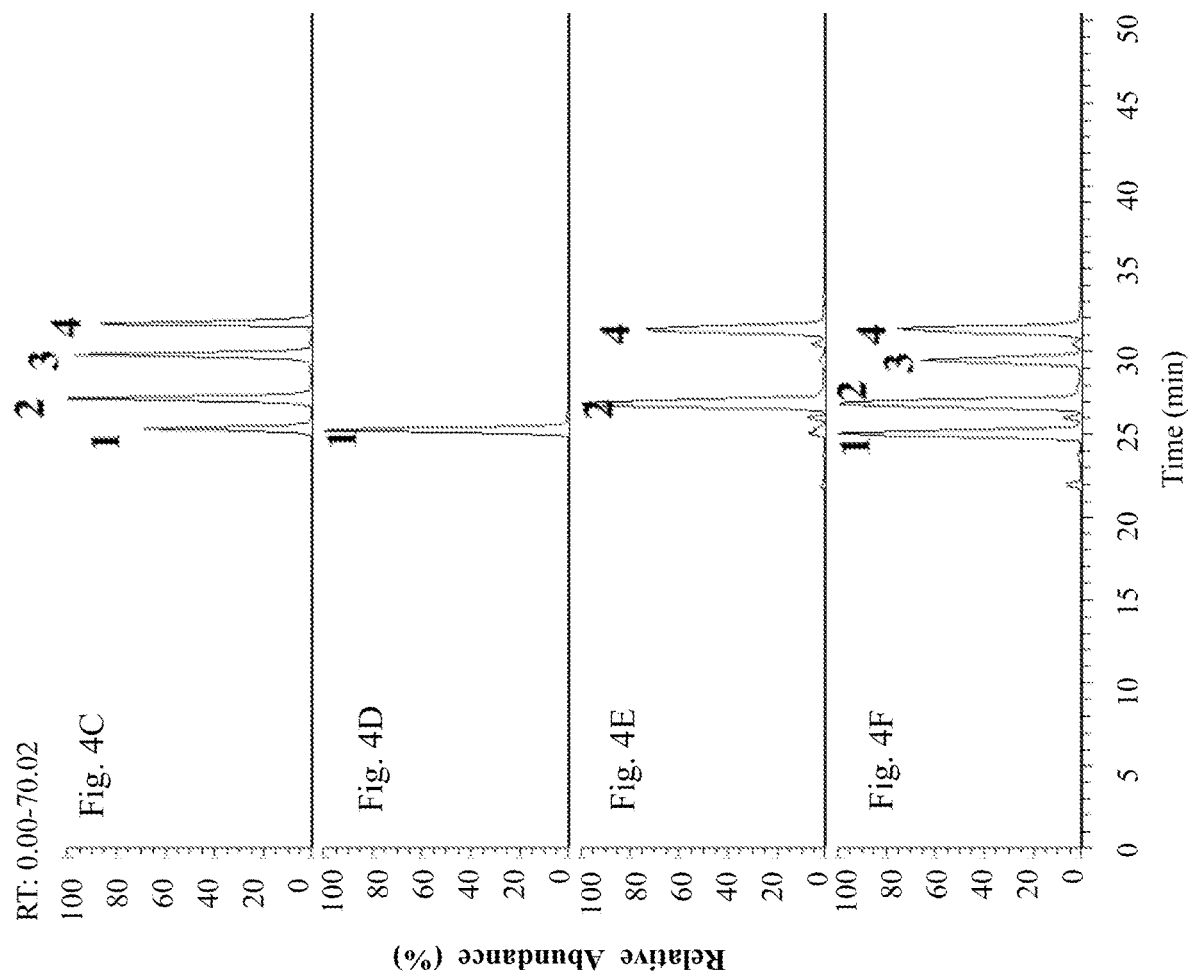

SEQUENCE LISTING

```
<160> NUMBER OF SEQ ID NOS: 2

<210> SEQ ID NO 1
<211> LENGTH: 54
<212> TYPE: DNA
<213> ORGANISM: artificial sequence
<220> FEATURE:
<223> OTHER INFORMATION: forward primer
<220> FEATURE:
<221> NAME/KEY: primer_bind
<222> LOCATION: (1)..(54)

<400> SEQUENCE: 1
ggggacaagt ttgtacaaaa aagcaggctt caccatgaag tttattttat tgtc       54

<210> SEQ ID NO 2
<211> LENGTH: 48
<212> TYPE: DNA
<213> ORGANISM: artificial sequence
<220> FEATURE:
<223> OTHER INFORMATION: reverse primer
<220> FEATURE:
<221> NAME/KEY: primer_bind
<222> LOCATION: (1)..(48)

<400> SEQUENCE: 2
ggggaccact ttgtacaaga aagctgggtc gaagctacac tggttagg             48
```

METHOD FOR BIOCONVERSION OF MOGROSIDE EXTRACTS INTO SIAMENOSIDE I

SEQUENCE LISTING

The instant application contains a Sequence Listing which has been submitted electronically in the ASCII text file and is hereby incorporated by reference in its entirety. The ASCII text file is a sequence listing entitled "2019-12-19-336-Seq-Listing" created on Dec. 19, 2019 and having a size of 4,096 bytes in compliance of 37 CFR 1.821.

BACKGROUND OF THE INVENTION

1. Technical Field

The present invention relates to a method for bioconversion of mogroside extracts. More particular, the present invention relates to a method for bioconversion of mogroside extracts into siamenoside I.

2. Description of Related Art

Global demands for natural sweeteners have significantly increased over the past decades due to concerns about long-term consumption of artificial sweeteners (NAS) as sugar substitutes. To date, the U.S. Food and Drug Administration has only approved two types of high-intensity natural sweetners, including purified *rebaudiana* A (from the leaves of *Stevia rebaudiana*) and mogroside extracts (from the fruit of *Siraitia grosvenorii*, commonly called Lo Han Kuo: LHK).

Mogrosides consist of a triterpenoid aglycone (mogrol) with different numbers of attached glucose molecules. The sweetness of mogrosides may be determined by the number and locations of the glucose moieties. For example, mogroside V contains five glucose moieties in its molecular structure and is 392 times sweeter than 5% sucrose in water. Moreover, Siamenoside I and mogroside IV have four glucose moieties each, but at different locations, and are respectively 563 and 465 times sweeter than 5% sucrose. On the other hand, mogroside III E, with three glucose moieties, is somehow less sweet. Indeed, siamenoside I is currently considered to be the sweetest mogroside. Additionally, the taste of siamenoside I was reported to be preferred over mogrosides IV and V; however, the amount of siamenoside I in natural mogroside extracts is limited. Thus, isolation, purification, or enrichment methods that can yield high concentrations of natural siamenoside I would be beneficial. Many attempts, including chemical hydrolysis, enzyme treatment, and microbial fermentation, have been made to convert mogroside V to siamenoside I. Unfortunately, the complexity of glucose branching side-chains in mogrosides makes the production or isolation of pure siamenoside I extremely challenging.

Exg1p in *Saccharomyces cerevisiae* is a glycoside hydrolase family 5 (GH5) enzyme, which is known to hydrolyze O-β-D-glycosidic linkages at the nonreducing end of polymer chains, resulting in the release of glucose. It has been found that substrates for Exg1p include flavonoid glucosides, such as naringenin 7-O-β-glucopyranoside and luteolin 7-O-glucoside, and Exg1p has been identified as the major exo-(1, 3)-β-glucanase involved in the initiation of mogroside bioconversion. During fermentation, Exg1p hydrolyzes mogroside V to create a mixture of siamenoside I and mogroside IV intermediates, with higher preference for mogroside IV. In wild-type *S. cerevisiae*, mogroside III E, is eventually generated as an end product.

It has been reported that there is 62 different enzymes for mogroside bioconversion, and out of those 62 enzymes, only β-galactosidase from *Aspergillus oryzae* (Sigma G5160) and dextranase from *Penicillium* sp. (Worthington DEXC) could enrich siamenoside I in mogroside extracts. The enrichment was reported to be up to 44% and 31% of all mogrol glucosides when the extract was treated with the specific microbial enzymes at 37° C., pH 5 for 7 h or at 37° C. pH 6 for 24 h, respectively. However, it is likely that these enzymes eventually convert mogroside V into MG III E or other mogrosides as end products. Another study showed that acid or alkali treatment of mogroside V produces nonspecific stereoisomeric mixtures of mogrosides and other byproducts, which are not desirable and exhibit low yields.

SUMMARY OF THE INVENTION

Since the family of GH5 enzymes is widely distributed across bacteria and fungi, with broad sequence diversity and protein specificity. There is a need in the art to find an Exg1-like enzyme from bacteria or yeast that may specifically produce siamenoside I from LHK mogroside extracts.

Therefore, the primary objective of the present invention is to provide a method for bioconversion of mogroside extracts into siamenoside I, comprising: using (1) DbExg1 protein or (2) a microorganism expressing the DbExg1 protein to contact or to cultivate with the mogroside extracts.

Further, the mogroside extracts is mogroside V.

Further, the microorganism is *Dekkera bruxellensis*.

Further, the microorganism is a yeast either containing a vector, wherein the vector carries DbExg1 gene or bearing a modification of promoter of native DbExg1 gene.

Further, the yeast is Exg1-deleted *S. cerevisiae*.

Further, the DbExg1 protein is a recombinant DbExg1 protein.

Further, the bioconversion is performed at pH 3.0 to 7.0.

Further, the bioconversion is performed at pH 5.0 to 7.0.

Further, the bioconversion is performed at a temperature ranging from 30 to 60° C.

Further, the bioconversion is performed at 50 to 60° C.

As above, comparing to the prior art, the present invention has the following advantages:

1. The method of the present invention converts the mogroside extracts into siamenoside I, which has a higher sweetening power and better taste than other mogrosides.

2. The present invention uses a microorganism expressing the responsible enzyme, DbExg1, which was identified in the present invention as a mediator of mogroside V conversion into siamenoside I, so that siamenoside I was preferentially produced.

Thus, the method of the present invention provides a feasible approach to produce large quantities of the natural sweetener, siamenoside I, which can then be applied in several industries, such as the beverage or baking industry.

BRIEF DESCRIPTION OF THE DRAWINGS

FIG. 1. is HPLC-MS chromatograms of mogrosides showing mogrol glycoside profiles after bioconversion by different yeast strains for 4 days. (FIG. 1D) *Kluyveromyces marxianus* (EC Hansen) van der Walt (FIG. 1E) *Saccharomyces pastorianus* (FIG. 1F) *Candida kefyr*

Figures 1A, 1B:
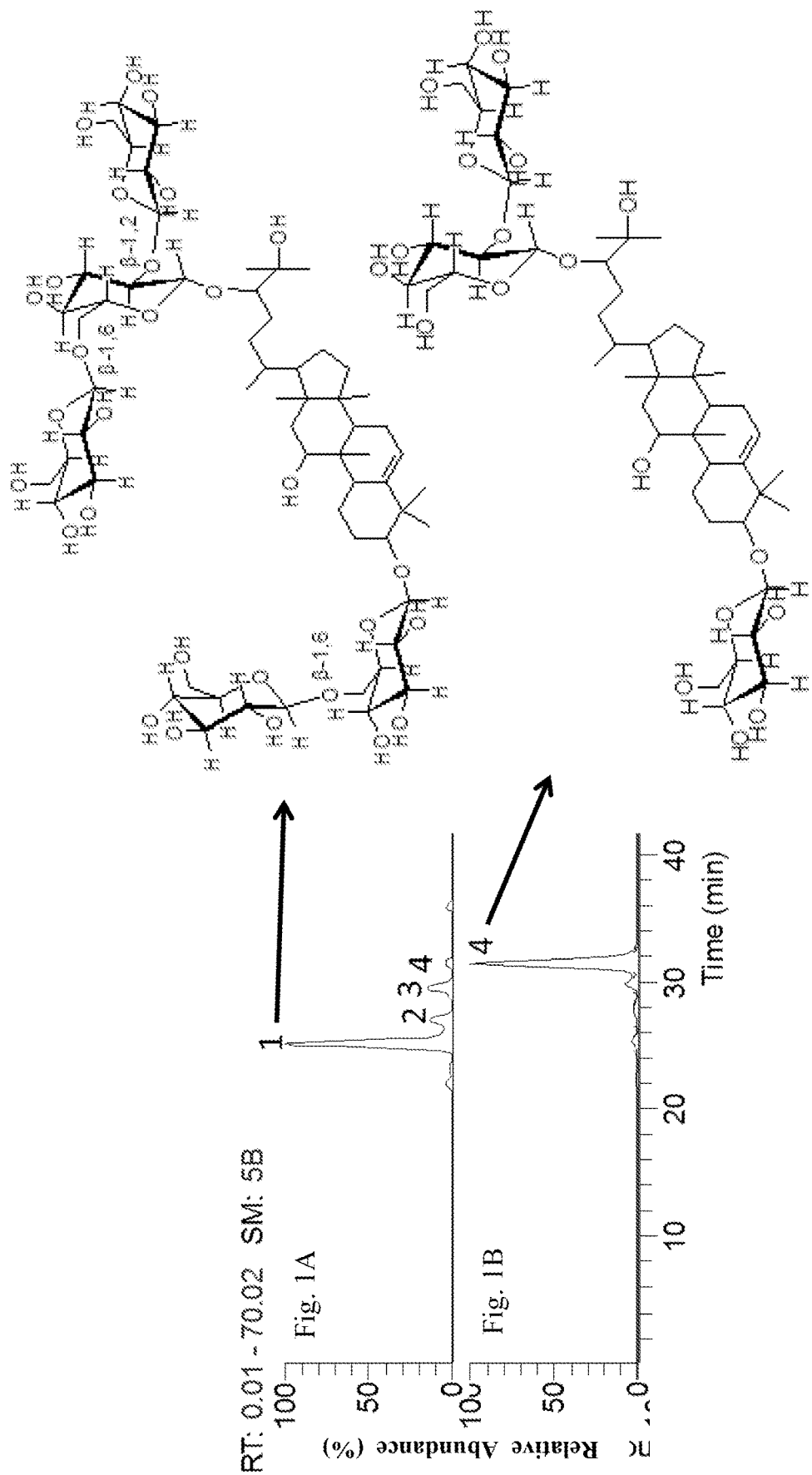
(FIG. 1A) Non-fermented mogroside extracts (FIG. 1B) *S. cerevisiae* las21Δ mutant (FIG. 1C) *S. cerevisiae* Meyen ex Hansen E. C.

(Beijerinck) van uden and Buckley (FIG. 1G) *Candida utilis* (FIG. 1H) *Yarrowia lipolitica* (FIG. 1I) *Debaryomyces hansenii* (FIG. 1J) *Dekkera bruxellensis*. Peak 1, mogroside V; Peak 2, siamenoside I; Peak 3, mogroside IV; Peak 4, mogroside III E. Arrows indicate the mogroside corresponding to the peak.

FIG. 2. shows cell growth of individual strains with or without 1% LHK extracts. (FIG. 2A) *S. cerevisiae* (FIG. 2B) *Debaryomyces hansenii* (FIG. 2C) *Yarrowia lipolitica* (FIG. 2D) *D. bruxellensis* were grown in YPD or YM media supplemented with or without 1% LHK extracts. Cell growth at different time points was determined by measuring the optical density at 600 nm with a spectrophotometer. Data are presented as the mean±SD from three independent experiments.

FIG. 3. shows characterization of recombinant ScExg1 and DbExg1. Recombinant enzymes were purified and the effects of pH (FIG. 3A and FIG. 3C) and temperature (FIG. 3B and FIG. 3D) on the stability and activity of recombinant ScExg1 (FIG. 3A and FIG. 3B) and DbExg1 (FIG. 3C and FIG. 3D) were determined. Data are presented as the mean±SD from three independent experiments.

FIG. 4. shows HPLC-MS/MS analyses of mogroside bioconversion. (FIG. 4A) The bioconversion of LHK extracts after induction of recombinant DbExg1 expression during fermentation. (FIG. 4B) The conversion of pure mogroside V by purified recombinant DbExg1 over 24 h of reaction at pH 5.0 in a 45° C. water bath. (FIG. 4C) Standard mogroside mix. (FIG. 4D) Non-fermented pure mogroside V. The conversion of pure mogroside V by (FIG. 4E) *D. hansenii* and (FIG. 4F) *Y. lipolytica*. Yeast were innoculated into culture media containing 1% pure mogroside V for 11 days of fermentation. Peak 1, mogroside V; Peak 2, siamenoside I; Peak 3, mogroside IV; Peak 4, mogroside III E.

DETAILED DESCRIPTION OF THE EMBODIMENT OF THE INVENTION

A detailed description and the technical contents of the present invention are given below with reference to the accompanying drawings. Furthermore, for easier illustrating, the drawings of the present invention are not a certainly the practical proportion and are not limited to the scope of the present invention.

Unless defined otherwise, all technical and scientific terms used herein have the same meaning as commonly understood to one of ordinary skill in the art to which this disclosure belongs. As used throughout the instant application, the following terms shall have the following meanings.

The use of "or" means "and/or" unless stated otherwise. The use of "comprise" means not excluding the presence or addition of one or more other components, steps, operations, or elements to the described components, steps, operations, or elements, respectively. Similarly, "comprise," "comprises," "comprising" "include," "includes," and "including" are interchangeable and not intended to be limiting. As used herein and in the appended claims, the singular forms "a," "an," and "the" include plural referents unless the context dictates otherwise. The terms "a", "an," "the," "one or more," and "at least one," for example, can be used interchangeably herein.

The present disclosure is directed to a method for bioconversion of mogroside extracts into siamenoside I, comprising: using (1) DbExg1 protein or (2) a microorganism expressing the DbExg1 protein to contact or to cultivate with the mogroside extracts.

"Mogroside" as used herein refers to natural mogroside sweeteners that have been used as a tabletop substitutes for sugar. In particular, mogroside III E and siamenoside I are known for their abilities to act as sweeteners and flavor enhancers. Siamenoside I is a minor compound in LHK and is normally present as an intermediate of mogroside metabolism during fermentation. In one preferred embodiment, the mogroside extracts is mogroside V.

Exg1 protein is the major exo-1,3-beta-glucanase in the cell wall of yeast. The aforementioned microorganism, in one preferred embodiment, is *Dekkera bruxellensis*. In one preferred embodiment, the microorganism is a yeast either containing a vector, wherein the vector carries DbExg1 gene or bearing a modification of promoter of native DbExg1 gene. In one preferred embodiment, the yeast is Exg1-deleted *S. cerevisiae*. In one preferred embodiment, the DbExg1 protein is a recombinant DbExg1 protein.

The bioconversion of the present invention can be performed at a preferred condition, for example without limitation, at a preferred pH and/or temperature. In one preferred embodiment, the bioconversion is performed at pH 3.0 to 7.0, such as pH 3.0 to 7.0, pH 3.0 to 6.5, pH 3.0 to 6.0. pH 3.0 to 5.5, pH 3.0 to 5.0, pH 3.0 to 4.5, pH 3.0 to 4.0, pH 3.0 to 3.5, pH 3.5 to 7.0. pH 3.5 to 6.5, pH 3.5 to 6.0, pH 3.5 to 5.5. pH 3.5 to 5.0, pH 3.5 to 4.5, pH 3.5 to 4.0, pH 4.0 to 7.0, pH 4.0 to 6.5, pH 4.0 to 6.0, pH 4.0 to 5.5, pH 4.0 to 5.0, pH 4.0 to 4.5, pH 4.5 to 7.0, pH 4.5 to 6.5, pH 4.5 to 6.0, pH 4.5 to 5.5, pH 4.5 to 5.0, pH 5.0 to 7.0, pH 5.0 to 6.5. pH 5.0 to 6.0, pH 5.0 to 5.5, pH 5.5 to 7.0, pH 5.5 to 6.5, pH 5.5 to 6.0, pH 6.0 to 7.0, pH 6.0 to 6.5, or pH 6.5 to 7.0. In a more preferred embodiment, the bioconversion is performed at pH 5.0 to 7.0, for example, pH 5.0, pH 5.1, pH 5.2, pH 5.3, pH 5.4, pH 5.5, pH 5.6, pH 5.7, pH 5.8, pH 5.9, pH 6.0, pH 6.1. pH 6.2, pH 6.3, pH 6.4. pH 6.5, pH 6.6, pH 6.7, pH 6.8. pH 6.9, or pH 7.0. In one preferred embodiment, the bioconversion is performed at a temperature ranging from 30 to 60° C., such as 30 to 60° C., 30 to 55° C., 30 to 50° C., 30 to 45° C., 30 to 40° C., 30 to 35° C., 40 to 60° C., 40 to 55° C. 40 to 50° C. 40 to 45° C., 45 to 60° C., 45 to 55° C., 45 to 50° C., 50 to 60° C., 50 to 55° C., or 55 to 60° C. In a more preferred embodiment, the bioconversion is performed at 50 to 60° C., such as 50° C., SC, 52° C., 53° C., 54° C., 5° C., 56° C., 57° C. 58° C., 59° C., or 60° C.

The present invention is more detailed illustrated by the example embodiments as below. While example embodiments are disclosed herein, it should be understood that they are used for illustrating the present invention, not for limiting the scope of the present invention.

Example 1

A. Experimental Section (1) Screening for Mogroside Conversion

Eighteen yeast strains and 13 lactic acid bacteria (LABs) (Table 1) were obtained from the Bioresource Collection and Research Center at the Food Industry Research and Development Institute (Hsinchu, Taiwan) for mogroside conversion screening. Mogroside extracts, containing 25.9% mixed mogrosides, were purchased from Changsha Huir Biological-tech Co., Ltd. (Hunan, China). Yeast or LABs were activated in yeast extract-peptone-dextrose (YPD, Difco, Sparks, Md., USA) or Man-Rogosa-Sharpe (MRS, Difco, Sparks, Md., USA) media, respectively. Media containing mogrosides were prepared by dissolving 1% (w/v) mogroside extracts in YPD or MRS broth. The yeast were aerobically cultured at 25° C. on an orbital shaker at 200 rpm, while LABs were anaerobically incubated at 37° C. The mogroside conversion was stopped by adding one volume of pure methanol to the culture media, and the mogroside content was analyzed by HPLC-MS/MS.

TABLE 1

Strain list

| Lactic acid bacteria | Yeast |
|---|---|
| *Lactobacillus plantarum* (BCRC10069) | *Candida maltosa* (BCRC 21482) |
| *Lactobacillus acidophilus* (BCRC10695) | *Candida utilis* (BCRC 21990) |
| *Lactobacillus bulgaricus* (BCRC10696) | *Candida kefyr* (Beijerinck) van uden & Buckley (BCRC 22057) |
| *Lactobacillus casei* (BCRC10697) | *Dekkera bruxellensis* (BCRC 21518) |
| *Lactobacillus rhamnosus* (BCRC10940) | *Dekkera bruxellensis* (mutant) |
| *Lactobacillus fermentum* (BCRC12190) | *Debaryomyces hansenii* (BCRC 21711) |
| *Lactobacillus paracasei* (BCRC12248) | *Kluyveromyces marxianus* (E C Hansen) van der Walt (BCRC 21499) |
| *Lactobacillus lactis* (BCRC12256) | *Kluyveromyces marxianus* (E C Hansen) van der Walt (BCRC 21696) |
| *Streptococcus thermophiles* (BCRC13869) | *Lachancea thermotolerans* (BCRC 23218) |
| *Lactobacillus kefir* (BCRC14011) | *Saccharomyces cerevisiae* BY4741 wild type |
| *Lactobacillus gasseri* (BCRC14619) | *Saccharomyces cerevisiae* BY4741 MATa his3Δ1 leu2Δ0 met15Δ0 ura3Δ0 exg1Δ::KanMX4 |
| *Lactobacillus reuteri* (BCRC14625) | *Saccharomyces cerevisiae* BY4741 MATa his3Δ1 leu2Δ0 met15Δ0 ura3Δ0 las21Δ::KanMX4 |
| *Sporolactobacillus inulinus* (BCRC14647) | *Saccharomyces cerevisiae* BY4741 MATa his3Δ1 leu2Δ0 met15Δ0 ura3Δ0 exg1Δ::KanMX4 pYES-DEST52 DbEXG1-6xHis-URA3 |
| | *Saccharomyces cerevisiae* (BCRC 21447) |
| | *Saccharomyces cerevisiae* Meyen ex Hansen E.C.(BCRC 21469) |
| | *Saccharomyces cerevisiae* Meyen ex Hansen E.C.(BCRC 23144) |
| | *Saccharomyces cerevisiae* Meyen ex Hansen E.C.(BCRC 23414) |
| | *Saccharomyces cerevisiae* Meyen ex Hansen E.C.(BCRC 23068) |
| | *Saccharomyces pastorianus* (BCRC 21423) |
| | *Yarrowia lipolytica* (BCRC 21490) |

(2) Mogroside Analysis by HPLC-MS/MS

Aliquots of fermentation media were first purified using solid phase extraction cartridges (C-18, 500 mg/3 mL, Chrome expert, Sacramento, Calif., USA). The unbound impurities were washed with 45% methanol, and the mogrosides were eluted with pure methanol. Fractions of the eluted mogrosides were collected for HPLC-ESI-MS/MS (YMC Hydrosphere C18 analytical column, YMC, Kyoto. Japan; Thermo Finnigan model LxQ linear ion trap mass spectrometer, San Jose, Calif., USA) analysis as described by previous study, with minor modifications. Ten microliters of the prepared samples was injected for mogrosides analysis. The following electron spray ionization (ESI) parameters were used: −4.8 kV spray voltage, 400° C. capillary temperature, 25 arb of sheath gas, 8 arb of auxiliary gas, 20% collision energy, and 2.0 Da isolation width. The mass scan range was 50-2000 m/z. Xcalibur 2.0.7 software was used for data analysis (San Jose, Calif., USA). The dominant molecular ions in the ESI/MS" spectra for mogrosides are $[M+Na]^+$; sequential glucose loss (−162 m/z) was observed in the fragmentation pattern in the collision-induced dissociation mode. Mogroside V, siamenoside I, mogroside IV, and mogroside III E were identified based on the presence of ions with m/values of 1309, 1147, 1147, and 985 for $[M+Na]^+$, respectively.

(3) Molecular Cloning, Expression, and Purification of Recombinant Protein

Exg1-like β-glucosidase from *Dekkera bruxellensis* (DbExg1) was cloned with the Gateway cloning system. Briefly, the coding region of DbExg1 was first amplified by PCR. The forward primer was (SEQ ID NO: 1)
5'-GGGGACAAGTTTGTACAAAAAAGCAGGCTTCAC<u>ATGAAGTTTATTT</u>

<u>TATTGTC</u>-3'.

underline indicates gene coding region). The reverse primer was (SEQ ID NO: 2)
5'-GGGGACCACTTTGTACAAGAAAGCTGGGTC<u>GAAGCTACACTGGTTAG</u>

<u>G</u>-3', underline indicates gene coding region). Genomic DNA extracted from *D. bruxellensis* was used as the template. Yeast expression vectors (pYES-DEST52) were further introduced to generate galactose-inducible plasmids carrying the correct DbExg1 sequence. The yeast vectors were then amplified and transformed into Exg1-deleted *S. cerevisiae* (exg1Δ mutants) for the galactose-induced DbExg1 protein expression assay. DbExg1 gene was also integrated into (exg1Δ mutants) with a GPD promoter. For protein purification, the culture media was concentrated with a 30 kDa MWCO (molecular weight cutoff) ultrafiltration membrane (Vivaspin 20, GE Co., Taipei, Taiwan). The extracellular protein concentrates were purified by $Ni^{2+}$-affinity chromatography. Protein homogeneity in each fraction was assessed by SDS-PAGE and silver staining.

(4) β-Glucosidase Activity and Mogroside V Conversion by Recombinant DbExg1

The optimal conditions for β-glucosidase activity were determined. The optimum pH was obtained by monitoring enzyme activity at a range of pH levels (from pH 3 to pH 9) in the reaction buffer. Incubation was carried out at 60° C. for 30 min. To analyze enzyme stability, the same buffer system and pH range were used, however, the reactions were performed at 4° C. for 1 h. The optimum temperature was determined in 20 mM acetate buffer at pH 5 in a range of temperatures from 20° C. to 90° C. For temperature stability analysis, β-glucosidase was extracted and activity was monitored following 1 h incubation in 20 mM acetate buffer, pH 5. Freshly purified rDbExg1 was added to 10 mM of β-nitrophenyl β-D-glucoside (pNPG), o-nitrophenol β-D-glucoside (oNPG) or authentic mogroside V (final concentration of 2 mg/mL) in acetate buffer solution. The enzyme and substrate mixture were incubated under optimum enzymatic reactions conditions of 60° C., pH 5. The f-glucosidase activity was determined by measuring the levels of p-nitrophenol (pNP) or o-nitrophenol (oNP) released from pNPG or oNPG after the glucose was hydrolyzed by glucosidase. The released pNP or oNP was detected at a wavelength of 405 nm and calibrated with standard curves. Mogroside conversion was stopped by the addition of one volume of pure methanol at specific time points. The converted products were then purified for HPLC-MS/MS analysis.

B. Results (1) Screening for Mogroside-Converting Strains

Several microorganism strains (18 yeast and 13 LABs) were selected for mogroside conversion testing, according to previous reports of glucosidase activity in the biotransformation of isoflavone. Mogroside extracts that mainly contained mogroside V were used as the bioconversion substrate (FIG. 1A). Surprisingly, none of the selected LABs exhibited mogroside bioconversion activity. In contrast, most of the yeast strains, which potentially play roles in bioflavoring, could convert mogroside V into a mixture of mogroside IV, siamenoside I and mogroside III E during 4 days of fermentation (FIG. 1D-G); Yarrowia lipolitica and Debaryomyces hansenii were the only two yeast strains that did not exhibit conversion activity (FIGS. 1H and I). S. cerevisiae with LAS21 deletion (las21Δ mutant) could completely bioconvertmogrosides V into mogroside III E (FIG. 1B) due to excessive leakage of Exg1 β-glucosidase and the efficient conversion of mogrosides. S. cerevisiae Meyen ex Hansen E. C. also efficiently converted mogroside V into mogroside III E (FIG. 1C) after 4 days of fermentation. Interestingly, only D. bruxellensis showed appreciable conversion of mogroside V into the siamenoside I intermediate (FIG. 1J), without a significant increase in the levels of mogroside IV and mogroside III E.

(2) D. bruxellensis is Unique for the Production of Siamenoside I.

Previous studies showed that α-amylase and protease secretion from bacteria can be regulated by growth stage and availability of nutrients. Thus, we questioned if slow cell growth could lead to low levels of secreted extracellular enzymes in the fermentation media, particularly in Y. lipolitica, D. hansenii and D. bruxellensis. Indeed, D. hansenii Y. lipolitica, and D. bruxellensis exhibited similar growth rates (FIG. 2 B-D), which were much slower than S. cerevisiae Meyen ex Hansen E. C. (FIG. 2A) and other S. cerevisiae strains (data not shown) in both YPD and YM media with or without mogroside extracts. However, D. bruxellensis was unique in that siamenoside I content steadily accumulated alongside the degradation of mogroside V, while the levels of mogrosides IV and III E were not significantly changed (FIG. 1J). Thus, our data do not rule out the possibility that the low bioconversion of mogrosides in Y. lipolitica and D. hansenii may result from low efficiency or different substrate specificity of the β-glucosidase enzymes in these cells.

Next, this Example extended the fermentation time to maximize bioconversion. We compared mogroside profiles in media fermented with various yeasts with or without crude mogroside extracts for 7 days (Table 2). The results showed that las21Δ mutants, which have a cell wall defect and release high levels of Exg1p into the media, could completely convert mogroside V into mogroside III E (Table 2). Similarly, S. cerevisiae Meyen ex Hansen E. C. (data not shown) and S pastorianus also convert mogroside V into mogroside III E. However, Kluyveromyces marxianus (EC Hansen) van der Walt, Candida kefyr (Beijerinck) van uden and Buckley and C. utilis could convert mogroside V into siamenoside I and mogroside III E after 7 days of fermentation (Table 2). Surprisingly, Y. lipolitica, D. hansenii and D. bruxellensis all exhibited poor conversion, resulting in the retention of substantial amounts of mogroside V and some amount of mogroside IV in the media after 7 days of fermentation (Table 2). The end fermentation products of D. bruxellensis contained the lowest percentages of mogroside IV (1.48±0.38%) and mogroside IIIE (10.74±1.13%). Although D. hansenii exhibited conversion profiles similar to those of D. bruxellensis, the percentages of mogrosides IV and IIIE were markedly increased compared to crude LHK extracts and D. bruxellensis fermentation media (Table 2). These results implied that D. hansenii may convert mogroside V in LHK extracts into both siamenoside I and mogroside IV, which would explain the observed gradual accumulation of mogroside IIIE. In contrast, D. bruxellensis seemed to possess a unique enzyme to hydrolyze mogroside V into the preferred product, siamenoside I, but not mogroside IV. Thus, the total percentages of mogroside IV and mogroside IIIE were similar (~12% of total mogrosides) to those in LHK extracts.

TABLE 2

Bioconversion of crude LHK extract by different yeasts after 7 days

| Strain | Mogrosides | | | |
|---|---|---|---|---|
| | MG V | SI | MG IV | MG IIIE |
| | Relative ratio (%)* | | | |
| Crude LHK (Non- fermentation) | 79.39 ± 0.82$^a$ | 8.30 ± 1.00$^d$ | 9.33 ± 0.55$^a$ | 2.99 ± 0.24$^e$ |
| Saccharomyces cerevisiae BY4741 las21Δ::KanMX4 | ND | ND | ND | 100.00 ± 0.00$^a$ |
| Kluyveromyces marxianus (EC Hansen) van der Walt (BCRC 21499) | ND | 60.19 ± 2.92$^a$ | ND | 30.81 ± 2.92$^c$ |
| Saccharomyces pastorianus (BCRC 21423) | ND | ND | ND | 100.00 ± 0.00$^a$ |
| Candida Kefyr (Beijerinck) van uden & Buckley (BCRC 22057) | ND | 38.05 ± 1.30$^c$ | ND | 61.95 ± 1.30$^b$ |
| Candida utilis (BCRC 21990) | ND | 59.05 ± 1.60$^{ab}$ | ND | 40.95 ± 1.60$^c$ |
| Yarrowia lipolytica (BCRC 21490) | 22.83 ± 6.55$^b$ | 53.25 ± 7.69$^b$ | 6.48 ± 3.13$^{ab}$ | 17.44 ± 6.79$^d$ |
| Debaryomyces hansenii (BCRC 21711) | 20.63 ± 0.34$^b$ | 61.24 ± 0.19$^a$ | 2.90 ± 0.30$^{bc}$ | 15.24 ± 0.83$^{de}$ |
| Dekkera bruxellensis (BCRC 21518) | 25.11 ± 2.19$^b$ | 62.67 ± 3.71$^a$ | 1.48 ± 0.38$^c$ | 10.74 ± 1.13$^e$ |

*The relative ratio of mogrosides was quantified using HPLC-MS. The data are shown as the mean ± standard deviation from three independent experiments and were analyzed by one-way ANOVA followed by Duncan's multiple range test. The values in the same column with different letters are considered significantly different (p < 0.05).
ND stands for not detected.

(3) Characterization of Exg1p of *D. bruxellensis*

Because mogrosides are known to be hydrolyzed by Exg1p in *S. cerevisiae* (ScExg1), we hypothesized that an Exg1-like glucan-β-glucosidase in *D. bruxellensis* (DbExg1) might be responsible for the observed mogroside conversion. To test this hypothesis, DbExg1 was cloned with a galactose-induced promoter sequence and six-histidine tag (6×His) at the C-terminus of the gene. The plasmids were transformed and expressed in *S. cerevisiae* as previously described. After 6 hr of galactose induction, Western blotting analysis showed that the DbExg1 protein size was slightly increased to ~55 kDa due to the 6×His tag (data not shown). The recombinant DbExg1 (termed rDbExg1) was purified by Ni$^{2+}$-affinity chromatography (data not shown).

Figure 3A:
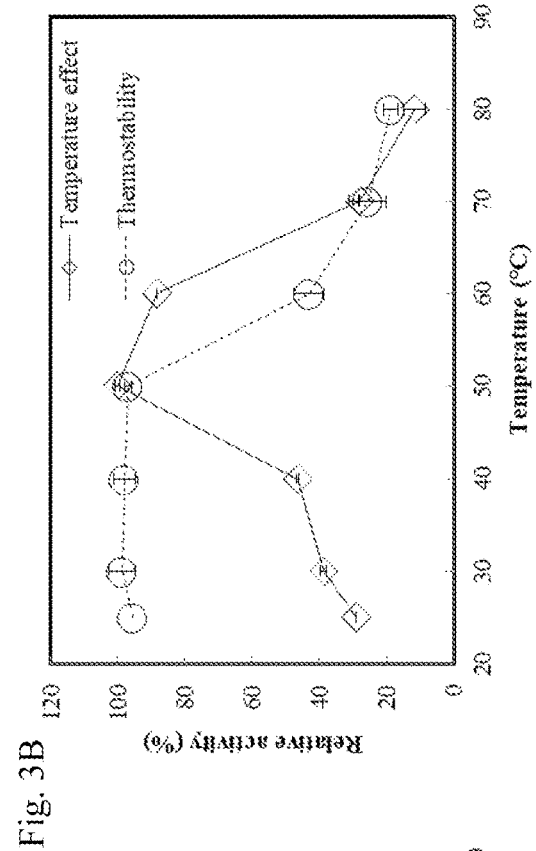
Figure 3B:
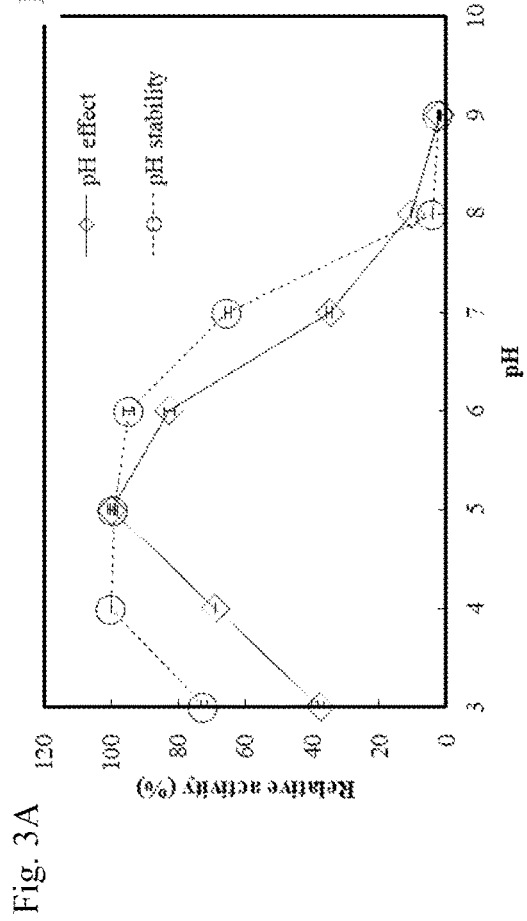
Figure 3C:
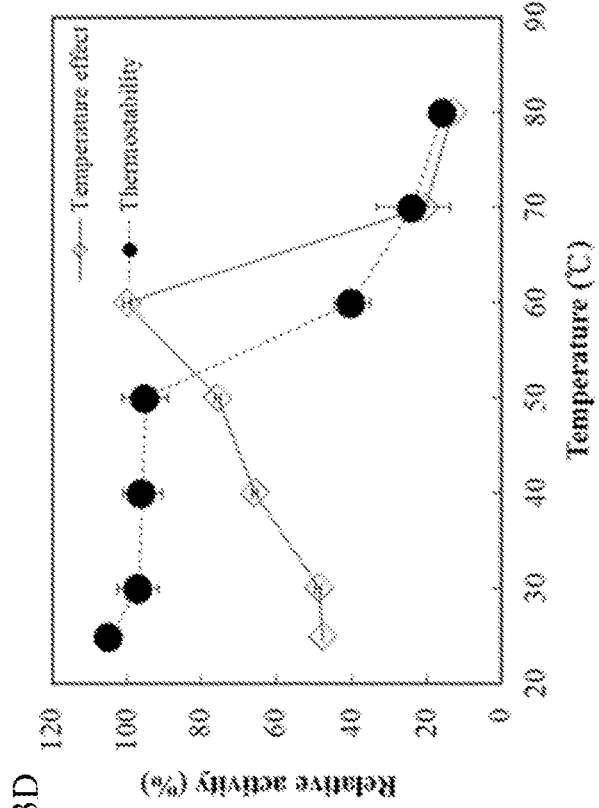
Figure 3D:
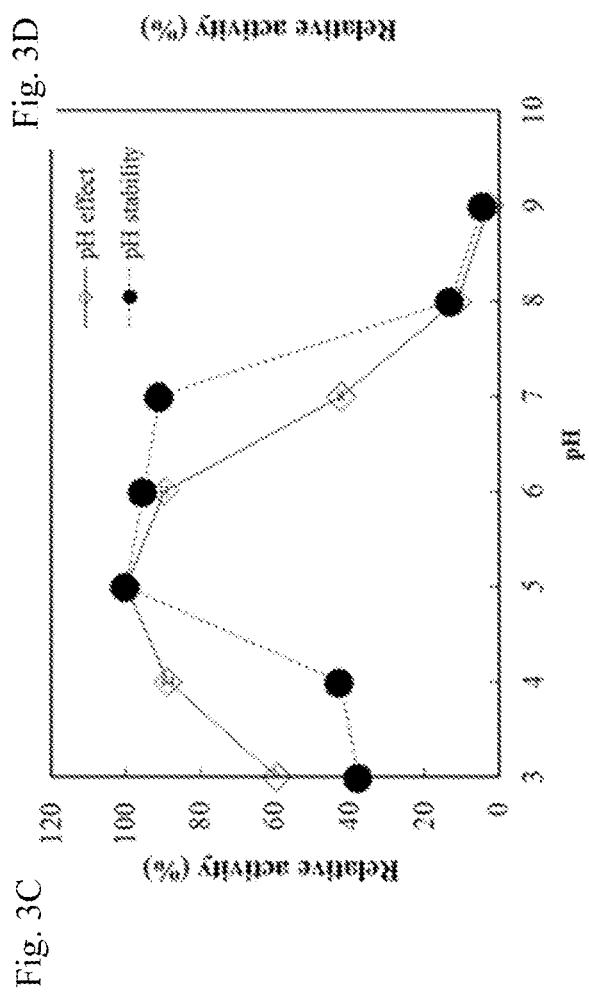

To evaluate the preferred pH, preferred temperature and hydrolyzing capability of rDbExg1, we used pNPG substrates and compared the results with ScExg1. rDbExg1 retained half of its activity over a pH range of 3.0 to 7.0 and was stable at pH 5.0-7.0. The optimum pH was 5.0 in a sodium phosphate buffer system (FIG. 3C). These results were similar to those from ScExg1 with slight differences in pH stability (FIG. 3A). The optimum temperature for rDbExg1 was 60° C. However, the enzyme only retained 40% of its activity after incubation at 60° C. for 30 min. In contrast, ScExg1 exhibited its highest hydrolyzing activity at 50° C. (FIG. 3B). Both ScExg1 and rDbExg1 were stable at temperatures below 50° C. (FIGS. 3B and D). The Michaelis constant ($K_m$) and maximum velocity ($V_{max}$) of rDbExg1 and rScExg1 were also compared and calculated (Table 3). Overall, the results indicated that rDbExg1 is a putative glucosidase that may hydrolyze the glucosidic bonds of oNPG and pNPG. Interestingly, no significant differences in enzyme kinetics were observed between rDbExg1 and ScExg1 with regard to oNPG and pNPG substrates (Table 3).

Table 3: Kinetic parameters of recombinant DbExg1 and ScExg1 proteins on oNPG and pNPG substrates (4) Enzymatic Hydrolysis of Mogrosides To test whether rDbExg1 may participate in mogroside conversion, this Example introduced plasmids carrying the rDbExg1 gene into the *S. cerevisiae* exg1Δ mutant, which cannot hydrolyze mogrosides. The expression of the extracellular rDbExg1 was easily

| Recombinant proteins | Substrates | $K_m$ (mM) | $V_{max}$ (μmol min$^{-1}$ mg$^{-1}$) | $K_{cat}$ (s$^{-1}$) | $K_{cat}/K_m$ (mM$^{-1}$s$^{-1}$) |
|---|---|---|---|---|---|
| rDbExg1 | o NPG | 0.781 ± 0.004 | 10.353 ± 0.046 | 0.518 ± 0.002 | 0.663 ± 0.001 |
| rDbExg1 | p NPG | 0.734 ± 0.002 | 9.273 ± 0.121 | 0.464 ± 0.006 | 0.632 ± 0.007 |
| rScExg1 | o NPG | 0.840 ± 0.042 | 9.16 ± 0.247 | 0.458 ± 0.012 | 0.546 ± 0.015 |
| rScExg1 | p NPG | 0.865 ± 0.003 | 11.73 ± 0.355 | 0.587 ± 0.018 | 0.679 ± 0.005 | detected after 9 hrs of galactose induction (data not shown). Indeed, the rDbExg1-transformed mutants not only regained the ability to convert mogrosides but also exhibited the ability to convert constituents of LHK extracts into siamenoside I with minor production of mogroside IIIE within 24 hr (FIG. 4A). Pure mogroside V was then used to examine whether rDbExg1 may bioconvert this molecule specifically into siamenoside I and test whether residual conversion to mogroside IIIE also occurs. As shown in (FIG. 4B), rDbExg1 could specifically hydrolyze the glucose moiety of β-1, 6 linkages at the C-3 position of mogroside V, resulting in the production of siamenoside I. Thus, the mogroside IIIE in LHK extracts fermented with *D. bruxellensis* (FIG. 4A) was most likely due to the presence of mogroside IV in the original LHK extracts. Notably, *D. hansenii* could bioconvert pure mogroside V into siamenoside I and mogroside IIIE (FIG. 4E), and *Y. lipolitica* could convert mogroside V into a mixture of mogroside IV, siamenoside I and mogroside IIIE after 11 days of fermentation (FIG. 4F). These results clearly demonstrated that the conversion of mogrosides and the production of siamenoside I in *D. bruxellensis* are unique among those strains we tested.

In summary, the present invention characterized an enzyme (DbExg1) that participates in this bioconversion by hydrolyzing the β-1, 6 glucopyranoside at C3, rather than the β-1, 6 glucopyranoside at C24 of mogroside V. The enzyme activity of DbExg1 was characterized according to its ability to hydrolyze the glucosidic bonds of oNPG and pNPG. The present invention also showed that *D. bruxellensis* has an uncommon ability to perform the bioconversion of mogroside V into siamenoside I.

Siamenoside I is a minor compound in LHK and is normally present as an intermediate of mogroside metabolism during fermentation. Through fermentation screening, it found that *D. bruxellensis* had extremely limited ability to fully hydrolyze mogrosides. As such, this strain converted LHK extracts from ~80% of mogroside V, ~8% siamenoside I, ~10% of mogroside IV and 3% of mogroside III E into ~86% of siamenoside I with 14% of mogroside III E. Based on the Example with purified mogroside V, it can conclude that the accumulation of mogroside III E is due to the conversion of mogroside IV (Table 2 & FIG. 4); fermentation of pure mogroside V through *D. bruxellensis* resulted in the production of siamenoside I only (FIG. 5).

In the present Example, we also compared DbExg1 to other yeast exoglucanases through enzyme clustering analysis (data not shown). The result shows that Exg1 proteins in the 18 tested yeast strains were closely related to DbExg1 glucanase and might have arisen from a common ancestral gene. However, the mogroside fermentation profiles were quite different among these strains. Intriguingly, some yeasts, such as *C. utilis*, preferentially accumulated mogroside IE as the major end fermentation product, while others, such as *C. kefyr* (Beijerinck) van uden and Buckley, favored siamenoside I production after 7-day fermentation of mogroside extracts (Table 2).

Together, these findings raised several possibilities. First, additional Exg1 homologs may exist in the yeast species we used in the Example. Thus, the production of mogroside IIIE or siamenoside I may be mediated by different Exg1 homologs. Indeed, in *S. cerevisiae*, there are three homologs with highly conserved exo-1,3-β-glucanase regions, including Exg1, Exg2 and Spr1. The previously research demonstrated that ScExg1 is responsible for mogroside bioconversion. In the present invention, DbExg1 was used to complement the *S. cerevisiae* exg1 mutant and showed the specific conversion of mogroside V into siamenoside I. Second, the Exg1 homologs may exhibit different enzyme specificities when mogrosides are provided as substrates. Thus, the catalytic discrepancies between strains may result from differences in substrate accessibility in the active site of the Exg1 homologs.

As above, comparing to the prior art, the present invention has the following advantages: the method of the present invention converts the mogroside extracts into siamenoside I, which has a higher sweetening power and better taste than other mogrosides; the present invention uses a microorganism expressing the responsible enzyme, DbExg1, which was identified as a mediator of mogroside V conversion into siamenoside I in the present invention, so that siamenoside I was preferentially produced. Thus, the use of the method of the present invention provides a feasible approach to produce large quantities of the natural sweetener, siamenoside I, which can then be applied in several industries.

The present invention is more detailed illustrated by the above preferable example embodiments. While example embodiments have been disclosed herein, it should be understood that other variations may be possible. Such variations are not to be regarded as a departure from the spirit and scope of example embodiments of the present application, and all such modifications as would be obvious to one skilled in the art are intended to be included within the scope of the following claims.

What is claimed is:

1. A method for bioconversion of mogroside extracts into siamenoside I, comprising:
   (1) contacting a *Dekkera bruxellensis* extracellular β-glucosidase (DbExg1) protein with the mogroside extracts, or
   (2) cultivating a microorganism expressing the DbExg1 protein with the mogroside extracts,
   thereby converting the mogroside extracts into siamenoside I;
   wherein the DbExg1 protein is *Dekkera bruxellensis* BCRC 21518 extracellular β-glucosidase,
   wherein the mogroside extracts comprise mogroside V, and
   wherein the DbExg1 protein converts mogroside V to siamenoside I.

2. The method of claim 1, wherein mogroside V is the main mogroside in the mogroside extracts.

3. The method of claim 1, wherein the microorganism is *Dekkera bruxellensis*.

4. The method of claim 1, wherein the bioconversion is by cultivating the microorganism expressing the DbExg1 protein with the mogroside extracts, wherein the microorganism is a yeast, and wherein the yeast comprises a polynucleotide encoding the DbExg1 protein or comprises a modification to the promoter of the native DbExg1 gene.

5. The method of claim 4, wherein the yeast is *Saccharomyces cerevisiae* with a deletion of an extracellular β-glucosidase.

6. The method of claim 1, wherein the DbExg1 protein is a recombinant DbExg1 protein.

7. The method of claim 1, wherein the bioconversion is performed at pH 3.0 to 7.0.

8. The method of claim 7, wherein the bioconversion is performed at pH 5.0 to 7.0.

9. The method of claim 1, wherein the bioconversion is performed at a temperature ranging from 30 to 60° C.

10. The method of claim 9, wherein the bioconversion is performed at 50 to 60° C.

* * * * *